Figure 1A:
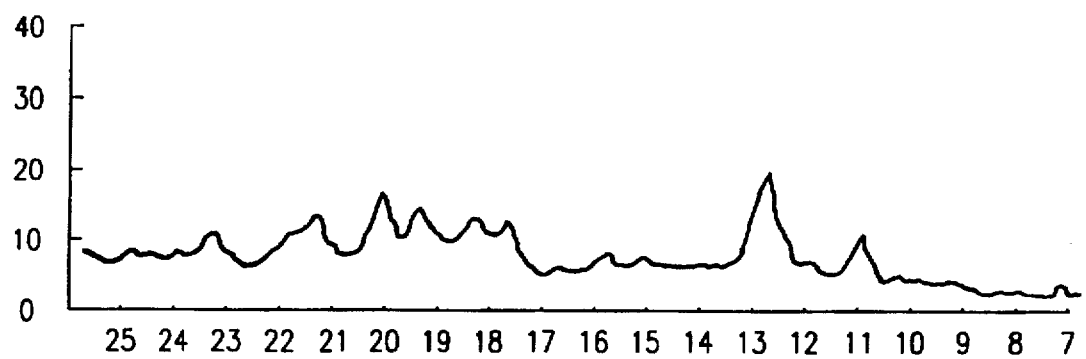

United States Patent [19]

Fischer et al.

[11] Patent Number: 5,665,767

[45] Date of Patent: Sep. 9, 1997

[54] CRYSTALLINE CYCLODEXTRIN COMPLEXES OF RANITIDINE HYDROCHLORIDE, PROCESS FOR THEIR PREPARATION AND PHARMACEUTICAL COMPOSITIONS CONTAINING THE SAME

[75] Inventors: Wilfried Fischer; Karin Klokkers, both of Holzkirchen, Germany

[73] Assignee: Hexal Pharma GmbH, Holzkirchen, Germany

[21] Appl. No.: 513,779

[22] PCT Filed: Mar. 4, 1994

[86] PCT No.: PCT/EP94/00645

§ 371 Date: Dec. 15, 1995

§ 102(e) Date: Dec. 15, 1995

[87] PCT Pub. No.: WO94/20091

PCT Pub. Date: Sep. 15, 1994

[30] Foreign Application Priority Data

Mar. 5, 1993 [HU] Hungary ................................. 93,6024

[51] Int. Cl.⁶ .......................... A61K 31/34; A61K 31/715

[52] U.S. Cl. ................................................ 514/471; 514/58
[58] Field of Search ..................................... 514/58, 471

[56] References Cited

FOREIGN PATENT DOCUMENTS

91/13100   9/1991   WIPO .

Primary Examiner—Raymond Henley, III
Attorney, Agent, or Firm—Burgess, Ryan & Wayne

[57] ABSTRACT

The present invention relates to cyclodextrin inclusion complexes of ranitidine hydrochloride which exhibit a novel, to date unknown crystalline structure, being significantly different from those of known "Form 1 and 2" and to the preparation of such inclusion complexes. The inclusion complexes are prepared from aqueous common solution or suspensions of ranitidine hydrochloride and cyclodextrin by removal of water. As complexing agents α-, β- and gamma-cyclodextrins, their alkylated, hydroxy alkylated derivates or their suitable mixtures are utilized. Finally, the invention concerns pharmaceutical compositions comprising the new complexes.

10 Claims, 3 Drawing Sheets

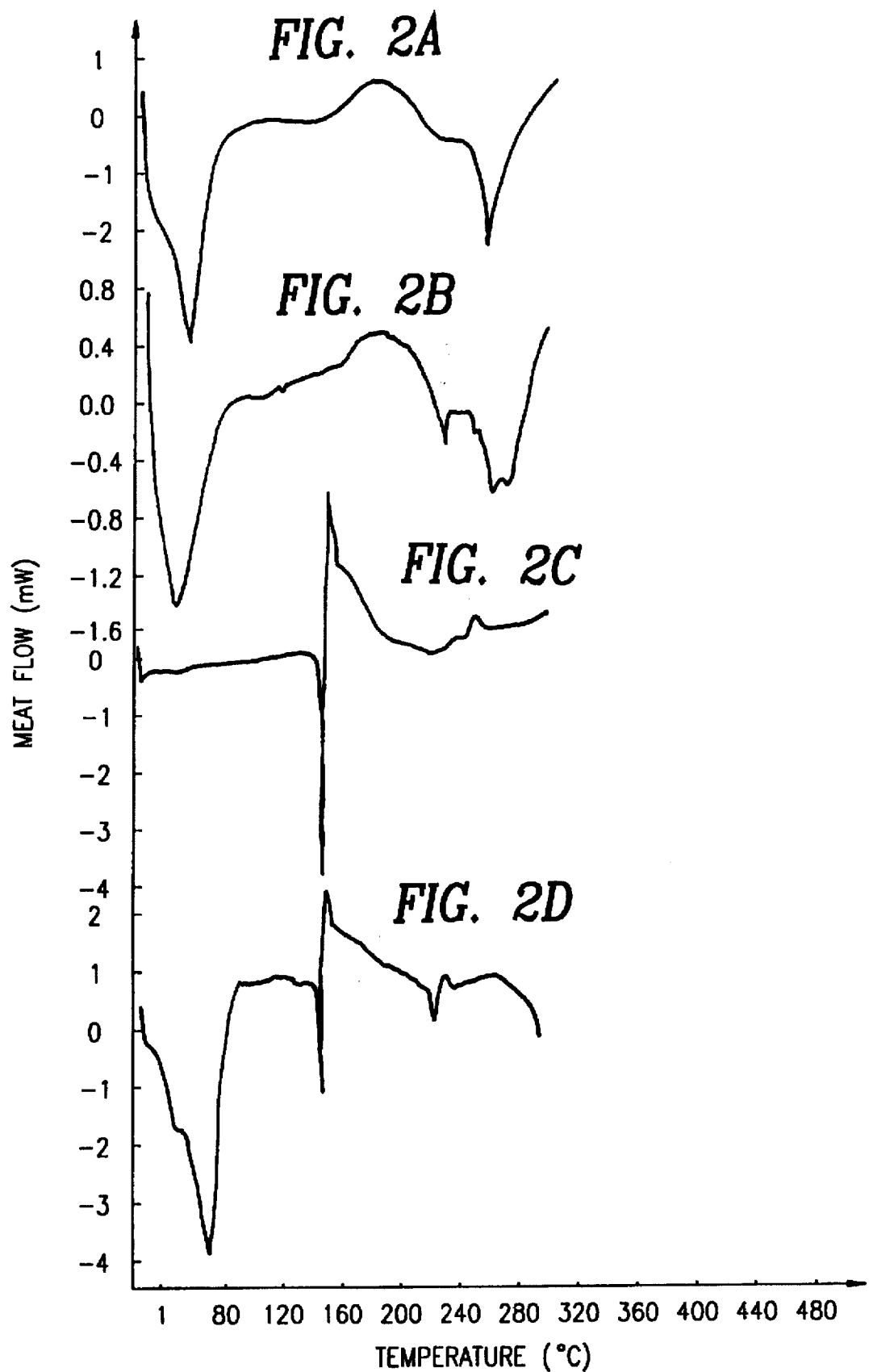

CRYSTALLINE CYCLODEXTRIN COMPLEXES OF RANITIDINE HYDROCHLORIDE, PROCESS FOR THEIR PREPARATION AND PHARMACEUTICAL COMPOSITIONS CONTAINING THE SAME

This application is a 371 of PCT/EP94/00645 filed Mar. 4, 1994.

The present invention relates to a novel type crystalline cyclodextrin inclusion complex of ranitidine hydrochloride, to the process for the preparation thereof, and to pharmaceutical compositions containing the same.

Ranitidine.HCl, i.e. N-[2(5-dimethylamino)methyl-2-furanylmethyl thio]ethyl-N-methyl-2-nitro-1-ethenediamine hydrochloride has been widely used as a histamine $H_2$ receptor atagonist for the treatment of gastric and duodenal ulcers, as well as for treating hyperacidic conditions. The substance inhibits the normal and stimulated secretion of gastric acid, thus it reduces the amount of gastric juice and its acid and pepsine content.

Two types of polymorphic crystalline forms of ranitidine.HCl, "Form 1" and "Form 2" have been described.

The basic form or "Form 1" can be obtained from the ethanolic solution of ranitidine base by salt formation with hydrochloric acid. The filtration and drying characteristics of "Form 1" are known to be unfavourable, moreover, it exhibits considerable hygroscopicity. "Form 2" is obtained upon the isopropanolic recrystallization of "Form 1".

The preparation of "Form 2" is described in U.S. Pat. No. 4,672,133. The two above crystalline forms of ranitidine-.HCl are well distinguishable by X-ray powder diffraction patterns, as their characteristic reflection peaks appear at different 2 theta angle values.

From a technological standpoint "Form 2" is more advantageous, consists of larger crystals, is easy to filter, to dry, and less sensitive to moisture.

Upon storage "Form 1" slowly gets converted into "Form 2".

The existence and spontaneous transformations of polymorphic forms of drug substances are of disadvantage, because they cause difficulties to fulfill exacting pharmaceutical requirements and specifications. The physicochemical properties of products with such polymorphics change according to the actual ratios of polymorphic forms.

Surprisingly, it has been found that strongly hydrophilic, in water freely soluble ranitidine hydrochloride formed a well defined crystalline inclusion complex with cyclodextrins, preferably with β-cyclodextrin.

According to one embodiment the invention concerns complexes of ranitidine hydrochloride as guest substance with cyclodextrin as host substance.

α-, β- and/or gamma-cyclodextrin and/or their alkylated and/or hydroxy alkylated derivatives are examples of cyclodextrin.

Further, ranitidine.HCl "Form 1" or ranitidine.HCl "Form 2" can be used as guest substance.

The molecular ratio of host substance: guest substance is normally $\geq 1$.

According to another embodiment the invention concerns a process for the production of complexes of ranitidine hydrochloride as guest substance with cyclodextrin as host substance, wherein an aqueous solution or suspension of the guest substance and the host substance is formed and the formed solution is brought to dryness, i.e. the water is removed. The aqueous solution of suspension has, for example, a content of 5 to 70 and especially 20 to 40% β-cyclodextrin. Ranitidine.HCl "Form 1" or ranitidine.HCl "Form 2" can be used as guest substance, or ranitidine base can be used as starting material for ranitidine hydrochloride as guest substance.

The water of the formed solution is, for example, removed by lyophilization, spray-drying, low temperature vacuum evaporation or vacuum drying.

Finally, according to one embodiment the invention concerns a pharmaceutical composition comprising as active ingredient their complex of ranitidine hydrochloride as guest substance with cyclodextrine as host substance beside usual ingredients and/or additives.

The above observation is surprising, since cyclodextrins have long been reputed to form crystalline inclusion complexes with guest molecules of a polar character, and of poor water solubility.

Both thermoanalytical studies (DSC: Differential Scanning Calorimetry) and X-ray powder diffractometry proved the existence of a novel solid phase and thus the formation of an inclusion complex.

The utilization of cyclodextrins for the complexation of poorly water soluble and absorbable drug substances, aiming at improved stability, water solubility and bioavailability has been described in literature. There have been known and discussed numerous practically used examples for the above purposes; cf. Szejtli, J., Cyclodextrin Technology, Kluwer Academic Publ., Dordrecht, 1988.

There has never been described in literature such unusual complexation of potential guests like the inclusion behaviour of ranitidine hydrochloride in the manner described in the present invention.

The water removal can be carried out by any known methods, i.e. spray drying, freeze drying or vacuum evaporation, vacuum drying or microwave treatment.

Since the complex formation is carried out preferably in an aqueous solution of ranitidine hydrochloride, there is no need to prepare the technologically more favourable "Form 2" for the complexation process.

For the complexation either "Form 1" and "Form 2" of ranitidine hydrochloride or even the ranitidine base can be used as the starting guest substance if the free base is transformed into their hydrochloride by using an equivalent amount of hydrochloric acid. This step moreover avoids the preparation of pure and highly crystalline ranitidine hydrochloride salts.

The ranitidine hydrochloride-β-cyclodextrin inclusion complex prepared according to the present invention is a microcrystalline almost white powder, that is less hygroscopic, and can directly be tabletted.

Even upon longer storage the molecularly ecapsulated (complexed) state of the drug excludes the possibility of any polymorphic transformation thus its utilization in solid pharmaceutical formulations proves more advantageous than that of the kown "Forms 1 and 2".

The preparation and characterization of the inclusion complex according to the present invention are illustrated by the following non-limiting Examples in details.

In the following the invention is described in greater details by means of examples and figures.

FIG. 1: X-ray powder diffractograms of ranitidine.HCl, of βCD and of inclusion complexes
A: ranitidine.HCl βCD complex according to example 1
B: ranitidine.HCl βCD complex according to example 3
C: ranitidine.HCl "Form 2"
D: β-cyclodextrin (βCD)

FIG. 2: DSC patterns of ranitidine.HCl of a mechanical mixture of the drug plus βCD and of inclusion complexes.
A: ranitidine.HCl βCD complex according to example 1
B: ranitidine.HCl βCD complex according to example 3
C: ranitidine.HCl "Form 2"
D: ranitidine.HCl βCD (mechanical mixture, 1:1 molar ratio)

Figure 3A:
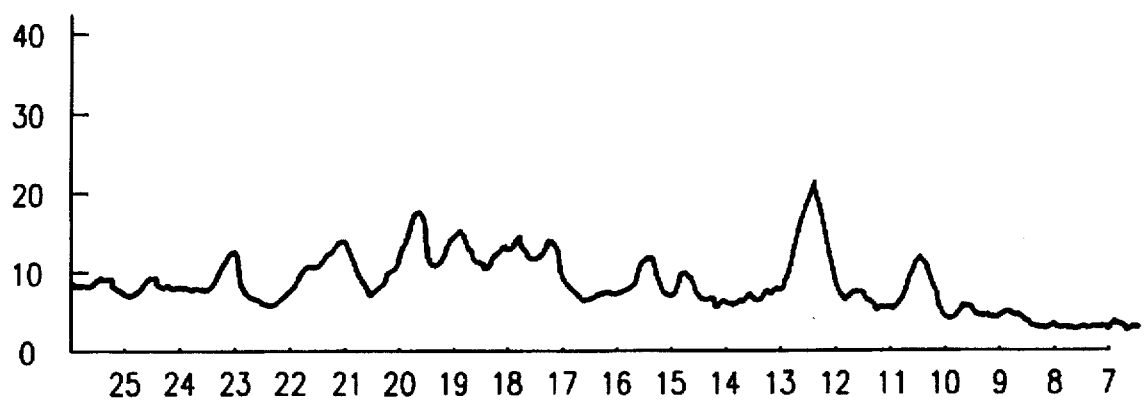
Figure 3B:
Figure 3C:
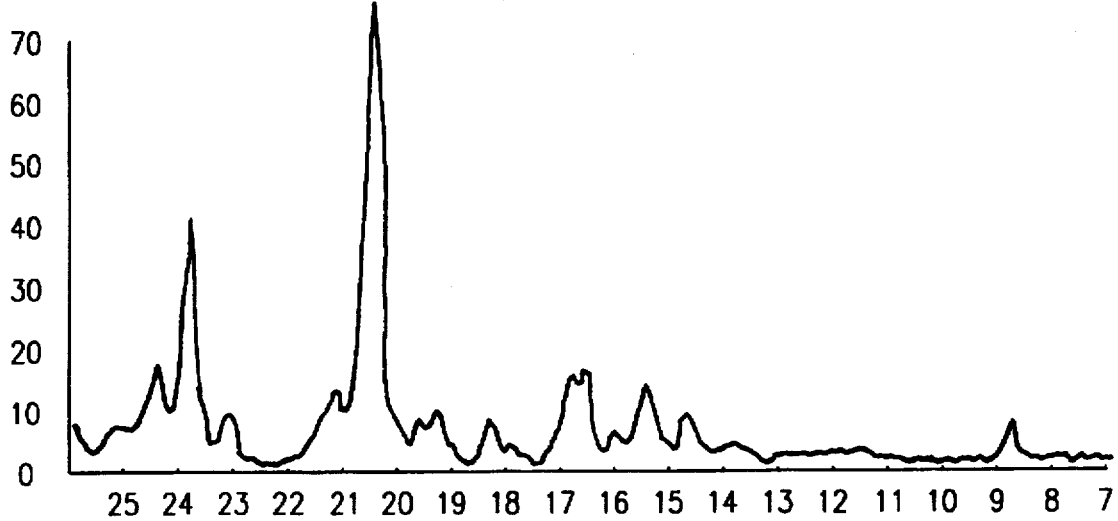

FIG. 3: X-ray powder diffractograms of ranitidine.HCl βCD complexes and ranitidine.HCl "Form 2"

A: ranitidine.HCl βCD complex (1:1)
B: ranitidine.HCl βCD complex (1:1) after 12 weeks storage at 76 % relative humidity
C: ranitidine.HCl "Form 2"

EXAMPLE 1

Preparation of the ranitidine hydrochloride-β-cyclodextrin complex 1:1 molar ratio:

0.7 g (2 mmoles) of ranitidine hydrochloride is dissolved in 5 ml of deionized water at ambient temperature. Then 2.6 g (2 mmoles) of β-cyclodextrin (water content: 14%) is added to the solution that is vigorously stirred until an almost clear solution is obtained. The resulting dense, honey-like suspension is freeze dried.

Yield: 3.1 g of beige powder with a ranitidine hydrochloride content of 21% by weight.

Characterization of complex obtained according to Example 1: The fact of complex formation is proved by X-ray powder diffraction pattern and DSC.

Figure 1B:
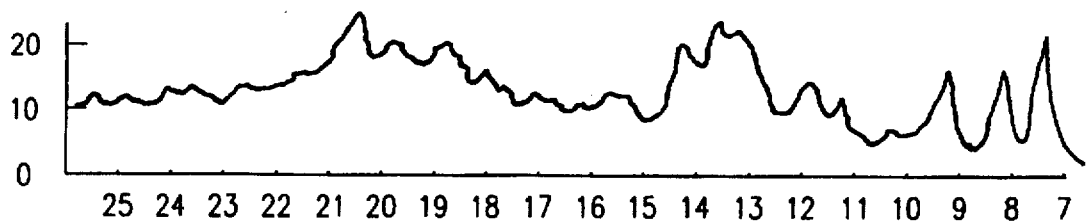
Figure 1C:
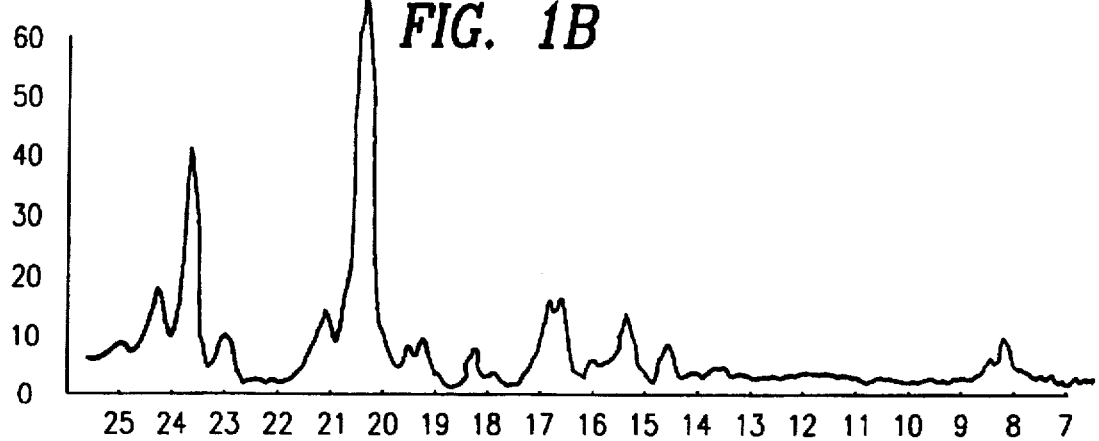
Figure 1D:
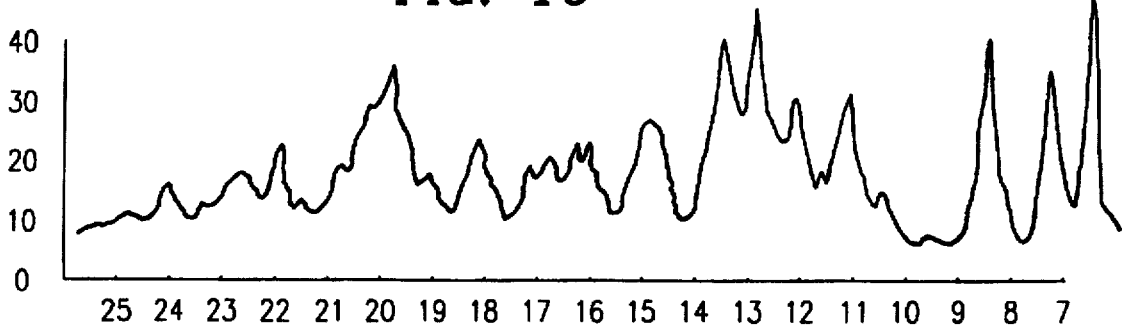

X-ray powder patters:

The X-ray diffraction pattern of complex (FIG. 1A) significantly differs from both the ranitidine-hydrochloride "Form 2" (FIG. 1C) and also differs from that of the identically treated β-cyclodextrin (FIG. 1D).

As seen in FIG. 1, the reflection peaks of the complex appear at different 2θ values as compared with those of ranitidine.HCl "Form 2" and β-cyclodextrin. The most characteristic 2θ angle values for the intense peaks of "Form 2" at 2θ°=20.2° and 23.4° completely disappear as a result of complex formation. This points indirectly to the generation of a novel, up to now unknown crystalline lattice of the ranitidine hydrochloride. By other words, this fact can be considered as a proof of the inclusion complex formation. (The most significant X-ray reflection peak data are listed in Table 1).

| Ranitidine.HCl ("Form 2") | β-cyclodextrin | Ranitidine.HCl βCD 1:1 complex | Ranitidine.HCl βCD 1:2 complex |
| --- | --- | --- | --- |
|  | 6,6 |  | 6,8 |
|  | 7,4 |  | 7,6 |
| 8,3 | 8,5 |  | 8,7 |
|  |  | 10,8 | 10,6 |
|  | 12,8 | 12,6 | 12,6 |
|  | 13,4 |  | 13,0 |
|  |  | 14,7 |  |
| 15,2 |  | 15,4 |  |
| 16,4 |  |  |  |
| 16,6 |  | 17,1 |  |
|  |  | 18,7 | 18,1 |
|  | 19,5 | 19,7 | 19,7 |
| 20,2 |  | 20,8 |  |
|  | 22,7 | 22,7 |  |
| 23,4 |  |  |  |

The characteristic reflection peaks of "Form 1" appear at different 2θ angle values (15.4, 16.8, 22.6, 24.2, 26.1) which are also significantly different from the reflection peaks of the inclusion complex according to Example 1.

Thermoanalytical investigations:

The DSC curves of ranitidine hydrochloride, of the complex and the corresponding mechanical mixture of the drug with β-cyclodextrin are shown in FIG. 2.

The sharp endothermic heat low peak characteristic for the melting of "Form 2" ranitidine.HCl is seen at 143°–145° C. (FIG. 2C), and this is the same on the DSC curve of the mechanical mixture (FIG. 2D).

The DSC pattern of the inclusion complex does not show any endothermic heat flow in the melting ranges indicating the formation of an inclusion complex between the drug and β-cyclodextrin (FIG. 2A).

EXAMPLE 2

Preparation of ranitidine.HCl-β-cyclodextrin complex of 1:1 molar ratio as in Example 1, but removing the water by vacuum drying:

Complex formation was carried out as described in Example 1. The dense suspension was dried under reduced pressure at ambient temperature to obtain the solid complex.

Yield: 3.1 g of beige powder with ranitidine.HCl content of 21% by weight.

For characterization of the complex, X-ray powder diffraction pattern was registered, which conforms with that one prepared by freeze-drying according to Example 1.

The complete disappearence of the most intense reflection peaks of ranitidine.HCl "Form 2" at 2θ=20.2 and 23.4 is also observed, slightly intense new peaks appear at 2θ=10.8, 12.6 and 19.7 values.

EXAMPLE 3

Preparation of ranitidide.HCl-β-cyclodextrin complex of 1:2 molar ratio:

0.7 g (2 mmoles) of ranitidine hydrochloride is dissolved in 5 ml deionised water. 5.2 g (4 mmoles) of β-cyclodextrin (water content 14%) is added to the solution which is stirred for 3 hours at room temperature intensively to provide the best possible solubility for β-cyclodextrin. The dense hardly stirrable suspension is then freeze dried.

Yield: 5.5 g of pale beige powder, with a ranitidine hydrochloride content of 12% by weight.

Characterization of the complex

X-ray powder diffractometry:

The powder diffractogram of the above complex is presented in FIG. 1B and this shows a significant difference between X-ray diffraction patterns of both the components and the complex of 1.1 molar ratio (FIG. 1A). The disappearance of the intense reflection peaks of the ranitidine.HCl "Form 2" can be seen also on the diffractogram of complex of 1:2 molar ratio.

Thermoanalytical investigations:

The DSC curve of the complex is shown in FIG. 2B. The vanishing of the melting endothermic peak refers to the entrapped state of drug in β-cyclodextrin according to Example 3.

EXAMPLE 4

Preparation of ranitidine.HCl-βCD of 1:1 molar ratio from ranitidine base:

132.0 g (0.42 mole) of ranitidine free base is mixed with 418 ml of 1M hydrochloric acid. 546 g (0.42 mole) of β-cyclodextrin (water content: 13.8%) is added to the solution. The mixture is vigorously stirred with magnetic stirrer for 2.5 hours. The dense honey-like suspension is then freeze dried. During the whole procedure the substance was protected from light.

Yield: 590±10 g pale beige powder, with ranitidine.HCl content of 22±0.5% by weight.

Thermoanalytical investigations:

On the DSC curve of ranitidine.HCl "Form 2" the characteristic melting endothermic peak appears at 143°–145° C. Such endothermic peak does not occur at all on the DSC curve of the complex according to Example 4, which points to the existence of an inclusion complex.

X-ray powder diffractometry:

The powder diffractogram of the complex is presented in FIG. 3A. The diffractogram of the complex is identical with that of prepared from ranitidine.HCl according to Example 1.

Storage stability test:

Complex sample prepared according to Example 4 was stored at 76% rel. humidity at room temperature for 12 weeks. X-ray diffractrogram of the stored sample was registered and is shown on FIG. 3B. The diffractogram of the sample showed no significant changes concerning the crystal structure, compared to the freshly prepared sample (FIG. 3A). The degree of crystallinity of the complex slightly increased, the ratio of peak intensities is slightly modified under storage at elevated humidity, however the characteristic peaks of ranitidine.HCl "Form 2" do not appear on the X-ray diffractogram after 12 weeks of storage.

EXAMPLE 5

Preparation of ranitidine.HCl-βCD complex of 1:1 molar ratio as in Example 4, but removing the water by vacuum drying:

Complex formation was carried out as described in Example 4. The dense suspension was dried under reduced pressure at ambient temperature to obtain the solid complex.

Yield: 3.9 g of pale beige powder with 21% ranitidine-.HCl content.

For characterization of the complex, X-ray powder diffraction pattern was registered, which was found to be indentical with that of the complex obtained according to Example 2.

EXAMPLE 6

A ranitidine.HCl-βCD granule sachet formulation with a 150 mg ranitidine base content pro dosage unit:

| Composition: | |
|---|---|
| Ranitidine.HCl βCD complex according to Example 1 | 800 mg |
| sorbit | 1500 mg |
| lemon flavour | 20 mg |
| saccharine | 5 mg |
| | 2325 mg |

The complex is homogenized with sorbite and additives then filled into dosing bags.

EXAMPLE 7

Ranitidine.HCl-βCD tablets with a 100 mg ranitidine base content:

| ranitidine.HCl βCD complex according to Example 5 | 500 mg |
|---|---|
| calcium phosphate | 80 mg |
| lactose | 45 mg |
| Mg-stearate | 5 mg |
| | 630 mg |

The complex is homogenised with the additives and directly pressed into tablets.

EXAMPLE 8

Preparation of ranitidine.HCl-βCD complex of 1:1 molar ratio from ranitidine base by spray-drying:

3.15 of ranitidine base (0.01 mol) is mixed with 10 ml of 1N hydrochloric acid solution. 13.0 g of β-cyclodextrin (0.01 mol, water content 13.8%) and 90 ml of distilled water are added to the solution. The mixture is stirred for an hour with magnetic stirrer, thereafter is spray-dried on Büchi 190 Mini-Spray-Dryer. Operating conditions:

Inlet temperature: 155° C.
Outlet temperature: 85° C.
Flow rate: 3–4 ml/min.

Yield: 5 g of pale-beige powder with ranitidine.HCl content of 22±0.5% by weight.

X-ray powder diffractometry. The powder diffractogram of the complex refers to a completely amorphous structure.

COMPARATIVE EXAMPLE 1

Samples of ranitidine.HCl-β-CD (according to Example 4), ranitidine.HCl-β-CD (according to Example 2), ranitidine.HCl "Form 1" and ranitidine.HCl "Form 2" were stored for 48 hours in water vapour saturated atmosphere at 20° C. The water uptake was measured and revealed the following results (water uptake in %)

| time [h] | ran.HCl-CD complex according to Ex. 1 | ran.HCl-CD complex according to Ex. 4 | ranitidine. HCl "Form 1" | ranitidine. HCl "Form 2" |
|---|---|---|---|---|
| 0 | 5,5 | 8,9 | 0,4 | 0,2 |
| 1 | 12,9 | 12,9 | 4,0 | 0,4 |
| 24 | 18,0 | not measured | >50 | not measured |
| 48 | 42,0 | 48,3 | >150 | 118,4 |

After 24 h and 48 h the complexes according to Examples 1 and 4 were solid powders whereas ranitidine.HCl "Form 1 and 2" had become syrup like liquids.

We claim:

1. Complexes of ranitidine hydrochloride as guest substance with β-cyclodextrin host substance.

2. Complexes according to claim 1, obtained by using ranitidine.HCl "Form 1" or ranitidine.HCl "Form 2" as guest substance.

3. Complexes according to claim 1, wherein the molar ratio of host substance: guest substance of is ≧1.

4. A pharmaceutical composition comprising as the active ingredient, a complex of ranitidine hydrochloride as the guest substance with β-cyclodextrine as the host substance including a pharmaceutically acceptable carrier.

5. A pharmaceutical composition according to claim 4 comprising as the active ingredient a complex of ranitidine hydrochloride and β-cyclodextrine, in the form of a tablet.

6. Process for the production of complexes of ranitidine hydrochloride as guest substance with β-cyclodextrin as host substance, wherein an aqueous solution or suspension of the guest substance and the host substance is formed and the water is removed.

7. Process according to claim 6, wherein an aqueous solution or suspension having a content of 5 to 70% β-cyclodextrin is formed.

8. Process according to claim 6 wherein ranitidine.HCl "Form 1" or "Form 2" is used as guest substance.

9. Process according to claim 6, wherein the water is removed by lyophilization, spray-drying, low temperature vacuum evaporation or vacuum drying.

10. Process according to claim 8 wherein a ranitidine base is converted to ranitidine hydrochloride and used as the guest substance.

* * * * *